United States Patent [19]
Wang et al.

[11] Patent Number: 5,315,254
[45] Date of Patent: May 24, 1994

[54] METHOD AND APPARATUS FOR NON-CONTACT CHARGE MEASUREMENT

[75] Inventors: Taylor G. Wang; Kuan-Chan Lin, both of Nashville; James C. Hightower, Franklin, all of Tenn.

[73] Assignee: Vanderbilt University, Nashville, Tenn.

[21] Appl. No.: 728,602

[22] Filed: Jul. 11, 1991

[51] Int. Cl.⁵ .............................................. G01N 27/60
[52] U.S. Cl. ................................... 324/452; 324/458; 324/72.5; 310/68 B; 310/309
[58] Field of Search ............... 324/452, 457, 458, 661, 324/662, 72, 72.5; 310/68 B, 308, 309

[56] References Cited

U.S. PATENT DOCUMENTS

| | | | |
|---|---|---|---|
| 4,300,298 | 11/1981 | Ehrat | 340/806 |
| 4,370,616 | 1/1983 | Williams | 324/457 |
| 4,424,481 | 1/1984 | Laroche et al. | 324/458 |
| 4,673,885 | 6/1987 | Lewiner et al. | 324/452 |
| 4,714,915 | 12/1987 | Hascal et al. | 324/457 |
| 4,825,147 | 4/1989 | Cook et al. | 324/678 |
| 4,928,057 | 5/1990 | Williams | 324/458 |

FOREIGN PATENT DOCUMENTS

| | | | |
|---|---|---|---|
| 661424 | 5/1979 | U.S.S.R. | 324/457 |
| 995016 | 2/1983 | U.S.S.R. | 324/452 |
| 1018052 | 5/1983 | U.S.S.R. | 324/457 |
| 1307395 | 4/1987 | U.S.S.R. | 324/457 |
| 1485157 | 6/1989 | U.S.S.R. | 324/457 |
| 1531031 | 12/1989 | U.S.S.R. | 324/72 |

Primary Examiner—Kenneth A. Wieder
Assistant Examiner—Glenn W. Brown
Attorney, Agent, or Firm—Stephen T. Belsheim

[57] ABSTRACT

A method and apparatus for the accurate non-contact detection and measurement of static electric charge on an object using a reciprocating sensing probe that moves relative to the object. A monitor measures the signal generated as a result of this cyclical movement so as to detect the electrostatic charge on the object.

8 Claims, 5 Drawing Sheets

METHOD AND APPARATUS FOR NON-CONTACT CHARGE MEASUREMENT

ORIGIN OF THE INVENTION

This invention was made with Government support under prime contract NASA NAS7-918, Task Order No. RE-4 subcontract NASA/JPL 958314 awarded by NASA. The Government has certain rights in this invention.

BACKGROUND OF THE INVENTION

The present invention relates to a method and apparatus to detect and measure a static electric charge on an object. More specifically, the invention concerns a method and apparatus for the accurate detection and measurement at a safe distance of a static charge on an object wherein the method and apparatus are applicable for experimental and industrial applications.

The detection and the measurement of static charge is one of the oldest problems experienced in both experimental work and in industrial applications. Although the problem has existed for some time, there has been little improvement in methods and apparatus used for static charge detection and measurement. This is especially true for non-contact static charge measurement.

Heretofore, there have been three basic methods commonly used for static charge measurement.

One basic method comprises the use of an electrostatic voltmeter. The use of an electrostatic voltmeter to measure the static charge has a major drawback because the probe of the electrostatic voltmeter has to contact the charged object. The contact may cause a spark. A spark could ignite a combustible atmosphere, such as that which exists in a chemical refining environment. The drawbacks and basic impracticality of using an electrostatic voltmeter become apparent.

Another method comprises establishing a force balance between a known electrical field and the charged object. However, the electrical field can only be applied to measure small non-fixed objects. Such limitations make the force balance method useless in real world applications.

The third method uses field mill instruments. For non-contact charge measurement, the field mill instruments (generating voltmeters) can sense the charge at a distance. However, present generating voltmeters are not true remote sensing instruments.

In a field mill instrument, the electric field is sensed through the sensing plate by applying a mechanical chopping device, i.e. a segmented rotor which is connected to the ground, to rotate in the front of the sensor. The change of the sensing area will then induce an alternating current which one can measure. The problem associated with this type of device is the inaccuracy of the measurement.

Two reasons cause this inaccuracy. First, the chopping process generates significant electronic noise which is difficult to filter. Electronic noise interferes with accurate measurement of a static charge. Second, for low voltage electric fields, the guard plate and chopping rotor used in these devices distort the field so much that very little of the actual field will impress on the sensor, hence, measurement cannot be performed accurately.

Because of accuracy problems, the measurement, which has an accuracy of no better than $10^4$ V/m, can only be done at a very short distance. In general, the measuring distance for a field mill instrument is less than one inch. For an electric field lower than $10^4$ V/m, it is very difficult to obtain an accurate measurement of the static charge with a field mill instrument. One example of a field mill generator is in Schwab, A.J., *High-Voltage Measurement Techniques*, pp. 141–146, The MIT Press, Cambridge, Mass. (1972).

Although static discharge does little harm to the human body, it can be detrimental in many situations. In some cases, industrial environments have explosive atmospheres. For example, a spark induced by a highly charged surface may trigger a dangerous explosion in chemical plants or petroleum refining facilities.

Industrial settings may include sensitive equipment. This delicate electronic equipment may be easily damaged by a static discharge. Further, the problem of static discharge has become more acute because of the wide applications of computer chips. A static discharge may easily damage computer chips.

It therefore becomes apparent that the ability to accurately and safely detect the build-up of high voltage static charge can be used to great advantage in laboratory and industrial situations. The accurate and safe detection of static charge can reduce the possibility of explosion in hazardous environments. It can reduce the possibility of damage to sensitive equipment including computers equipment including computer chips.

SUMMARY OF THE INVENTION

An object of this invention is to provide an improved method and apparatus for accurate non-contact static charge detection and measurement.

It is another object of the invention to provide an improved method and apparatus for accurate non-contact static charge detection and measurement that measures the static charge at a safe distance.

It is an object to provide an improved method and apparatus for accurate non-contact static charge detection and measurement which eliminates the potential hazards of generating undesired sparks triggered by static discharge.

It is an object of the invention to provide a faster, simpler and safer method and apparatus to accurately detect and measure static charge so that with proper calibration, high accuracy may be achieved, which is useful for laboratory experiments.

In one form thereof, the invention is an apparatus for the detection and measurement of static electric charge on the surface of a charged object. The apparatus comprising a sensing probe positioned a specified distance from the surface of the object. A motor means, connected to the sensing probe, for providing cyclic movement to the sensing probe so as to cyclically move the sensing probe relative to the surface of the object. A monitoring means, connected to the sensing probe, for monitoring the potential of the charged object.

In another form thereof, the invention is a method for the detection and measurement of static charge on a charged object. The method comprises the steps of positioning a sensing probe a specified distance from the surface of the object. Next, moving the sensing probe in a cyclic motion with respect to the surface of the object. Finally, monitoring the output signal from the sensing probe to determine the potential of the object.

BRIEF DESCRIPTION OF THE DRAWINGS

The drawing which are a part of this patent application are briefly described below.

DETAILED DESCRIPTION OF SPECIFIC EMBODIMENTS

Figure 1:
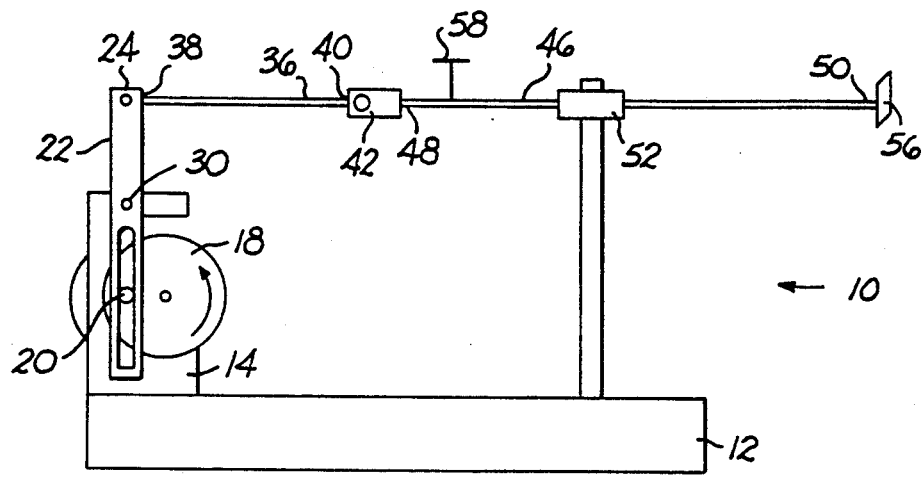
FIG. 1 is a mechanical schematic view of one specific embodiment of the present invention.

According to Gauss's Law, when a charge exists on an object, it sets up a related electrostatic field in the surrounding space. In the absence of other interference or at the near region of the object where the interference can be neglected, the strength of this field may be used to determine the charge quantity of the object.

By Gauss's Law, a conducting surface will acquire a net surface charge in an electric field if it is in electric contact with the ground. The amount of charge induced by an electric field depends on the field strength of the charged object, distance between the charged object and the conductor, and the geometry of the conductor.

By varying any one of the parameters, the charge on the conductor will change, and hence, a transient current will occur between the ground and the conductor. If the variation of distance between the charged object is controlled and the geometry of the conductor is fixed, then a defined current flow can be obtained.

To the best of the inventors' knowledge, the theory behind the operation of the present invention is shown by examination of the following equations applicable to the case of a point charge near a grounded sphere. The equation for an induced electrical charge between a point charge Q and a grounded conducting sphere is shown below:

$$Q' = -(a/D)Q$$

where Q is the point charge, D is the distance between the point charge and the center of the sphere, and a is the radius of the sphere. See Corson, D.R. and Lorrain, P., *Introduction to Electromagnetic Fields and Waves*, San Francisco and London: W.H. Freeman and Co., 1962, pp. 136–137.

As the sphere is set to a cyclic motion with an amplitude equal to "d", the induced charge on the sphere, Q', is shown by the following equation:

$$Q' = -[a/(d + d\cos\omega t)]Q$$

The current is then given by the equation:

$$I = dQ'/dt = [(d\omega a \sin\omega t)/(D + d\cos\omega t)^2]Q$$

Referring to the application of this principle to this invention, it is seen that the current output will vary as a function of the magnitude of the static charge on the surface of the charged object.

This current signal, although small, is detectable. For example, the conductor can be connected to the ground through a very high value resistor, and a high input impedance voltage measuring device, such as a digital multimeter or chart recorder, can then be used to measure the voltage change through the resistor. By quantifying this signal, the electric potential of the charged object can be accurately determined. It is upon this principle that the present invention operates.

To solve the problems associated with old field mill devices, a novel approach is needed, and the present invention provides this solution. In the present invention, the electrical signal pick up is done through a change in position of the sensor, but instead of chopping, the sensor is directly exposed to the electric field so as to maximize the current flow. When the sensing probe is brought to a charged object at a known distance, a transient signal will be picked up. By providing a cyclic relative motion between the sensor and the charged object, a cyclic signal will be produced.

As described with respect to these specific embodiments, this cyclic relative motion may be either reciprocal or rotational. However, any other cyclic motion will be satisfactory to carry out the invention.

When the sensor oscillates or rotates while keeping the reference distance between the probe and the measured object constant, the resulting output is an AC signal with the frequency defined by the oscillation or rotation of the sensor. In most of the cases, the output signal is weak and a higher input impedance device will be needed in order to get a higher output from the sensor. To achieve the same output amplitude for different voltage measuring devices and higher resolution, a high gain, high impedance amplifier is used to buffer and to boost the output signal from the sensing probe.

Figure 2:
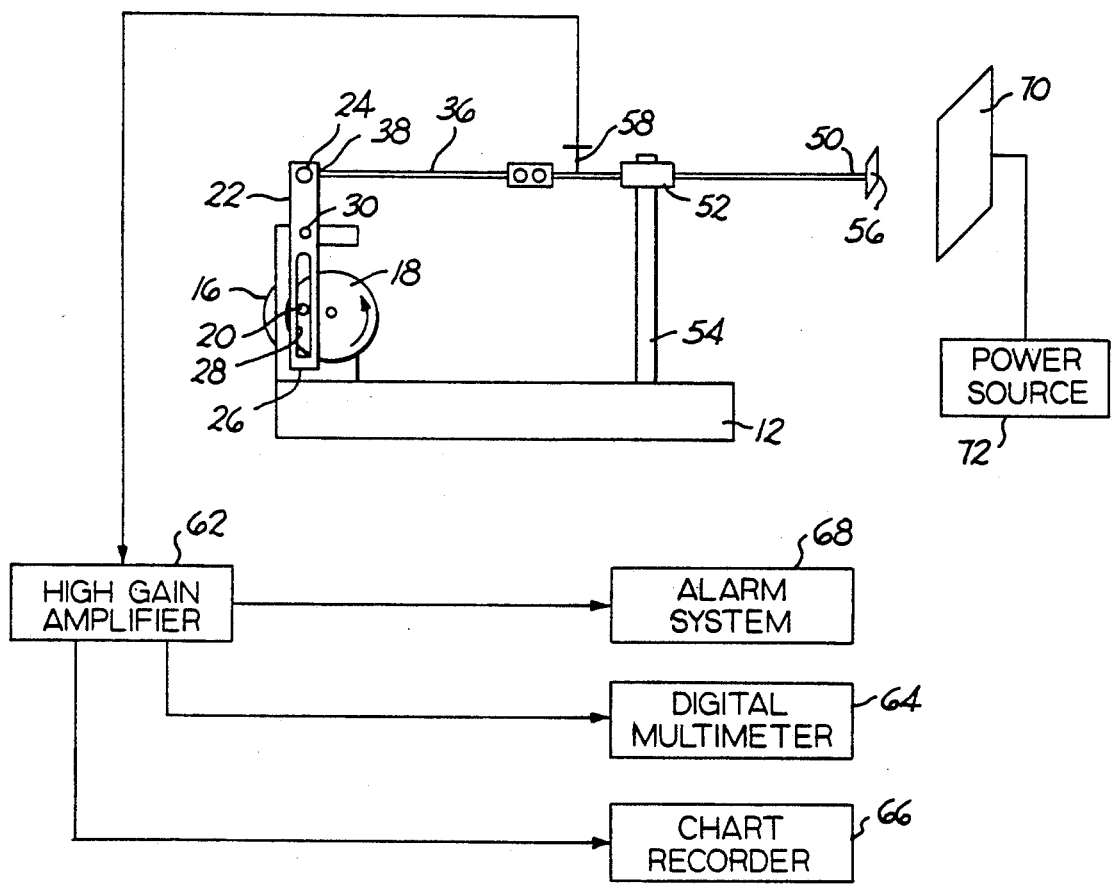
FIG. 2 is a mechanical schematic view showing the operation of the specific embodiment of FIG. 1.

FIGS. 1 and 2 illustrate one specific embodiment of a measurement apparatus, generally designated as 10. This embodiment has particularly good application to measure in a directional fashion towards a particular object. This embodiment essentially aims at an object thereby reducing interference from extraneous sources.

Measurement apparatus 10, includes a base 12 having a motor mount 14 mounted thereto. Motor mount 14 mounts a clock motor 16 which drives a wheel 18 with a protruding pin 20.

An elongate bar 22 has opposite upper and lower ends 24, 26 and contains an elongate slot 28 near the lower end 26 thereof. Elongate bar 22 pivotally mounts to motor mount 14 at pivot point 30.

A rod 36, made of a metal such as brass, has opposite ends 38, 40. Rod 36 pivotly connects at end 38 thereof to bar 22. Rod 36 pivotly connects at end 40 thereof to a linkage 42. Linkage 42 is made of an insulative material. Another rod 46, made of conductive material, has opposite ends 48, 50. Rod 46 connects at end 48 thereof to linkage 42.

Rod 46 passes through guide 52, which post 54 supports. Guide 52 is made from an insulative material.

A sensing probe 56, made of electrically conductive material, affixes to end 50 of rod 46.

A signal output 58 attaches to rod 46 adjacent end 48. Signal output 58 electrically connects to a high gain amplifier 62 which, in turn, connects to a digital multimeter 64 and a chart recorder 66, and alarm system 68.

In operation, the clock motor 16 rotationally drives wheel 18. Due to the engagement of pin 20 in elongate slot 28, the rotation of wheel 18 causes bar 22 to cyclically pivot about pivot point 30. The cyclical pivotal movement of bar 22 causes rods 36 and 46 to move reciprocally. This causes sensing probe 56 to move in a cyclic reciprocal fashion with respect to surface 70 thereby causing a cyclic signal. Surface 70 has a surface charge thereon caused by the connection to power source 72. This cyclic signal is an AC signal with the frequency defined by the oscillation of sensing probe 56. Because the signal is weak, a high input impedance device results in a higher output from the sensor.

To achieve the same output amplitude for different measuring devices and higher resolution, a high gain, high impedance amplifier is used to buffer and to boost the output signal from the sensing probe. The output signal feeds to the digital multimeter 64 and the chart recorder 66 so as to provide a visually perceptible output.

In addition, the output signal may go directly to an alarm system 68. In this type of arrangement, the alarm system may be in one condition when the static charge on the surface 70 is below a preselected value. When the static charge on the surface 70 exceeds a preselected value, the output reflects this fact, and the alarm system 68 is triggered thereby indicating that the static charge has exceeded the preselected value. In response to the output, the alarm system 68 may either sound an alarm or take action to discharge the object to a lower selected value.

Figure 3:
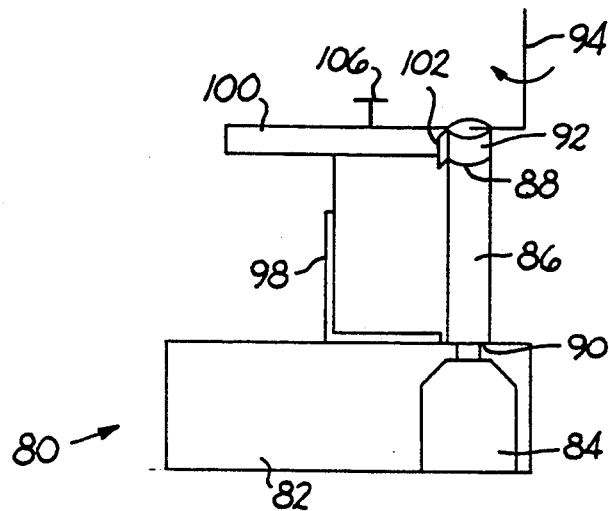
FIG. 3 is a mechanical schematic view of another specific embodiment according to the present invention.
Figure 4:
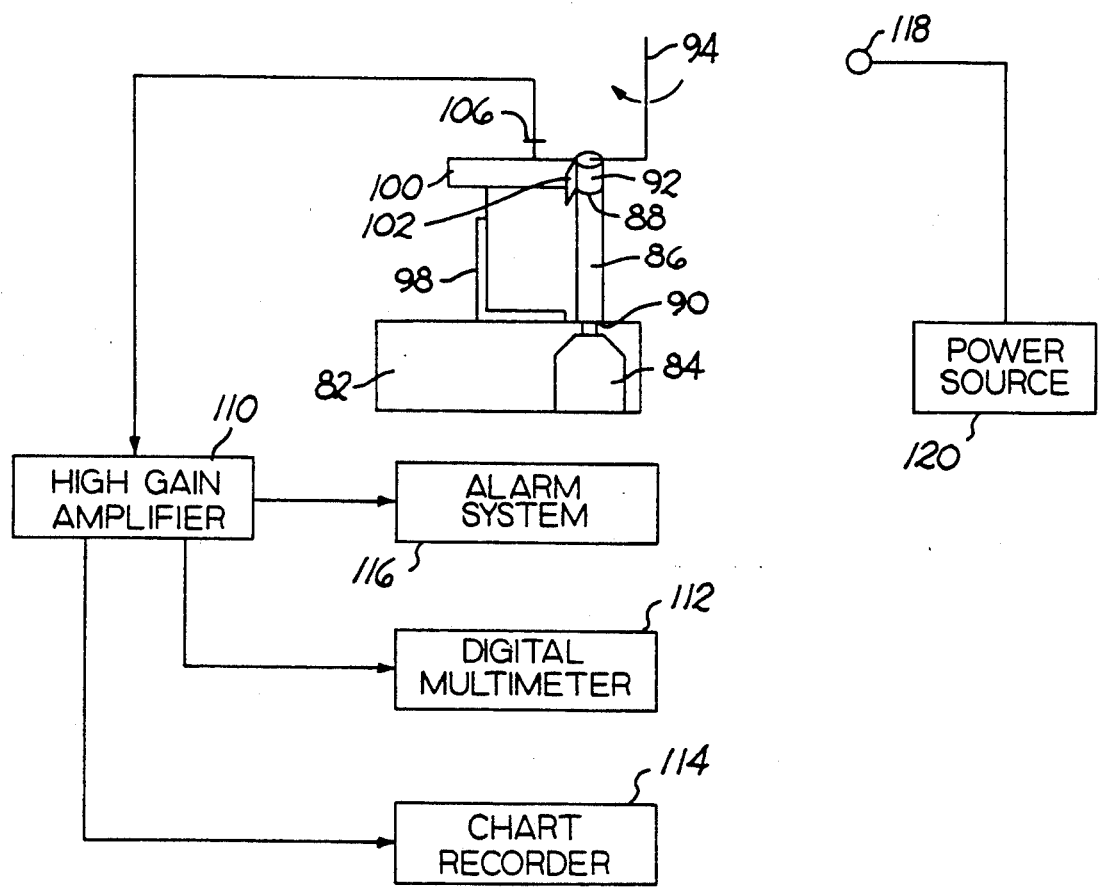
FIG. 4 is a mechanical schematic view showing the operation of the specific embodiment.

Referring to FIGS. 3 and 4, these drawings illustrate another specific embodiment of the invention. Measurement apparatus 80 includes a base 82. A motor 84 mounts to base 82. A rod 86, made of an electrically insulative material, and having opposite ends 88, 90 is attached to the shaft of motor 84. An electric conductor 92 mounts to the distal end 88 of rod 86. A rod 94, which acts as the sensing probe, affixes to the conductor 92.

A support 98 mounts to base 82. Support 98 provides support to insulator 100. A metal member 102 affixes to the end of insulator nearest sensing probe 94.

The metal member 102 connects to signal output 106, and signal output 106 connects to the high gain amplifier 110 which, in turn, connects to the digital multimeter 112, the chart recorder 114, and the alarm system 116.

In operation, the motor 84 rotates the shaft 86 and in turn the conductor and sensing probe 94. Sensing probe 94 is attached to conductor 92 which slidably contacts metal member 102 (which is a brush) during the rotation of the shaft 86.

This causes sensing probe 94 to move in a cyclic rotational fashion with respect to ball 118 thereby causing a cyclic signal. Ball 118 has a surface charge thereon caused by the connection to power source 120. This signal is an AC signal with the frequency defined by the oscillation of sensing probe 94. Because the signal is weak, a high input impedance device results in a higher output from the sensor.

The output is received by the digital multimeter 112, chart recorder 114 and alarm system 116. The digital multimeter 112 and the chart recorder 114 provide a visible way to monitor the output, which reflects the static charge. The alarm system 116 functions the same way as does the alarm system 68.

Figure 5:
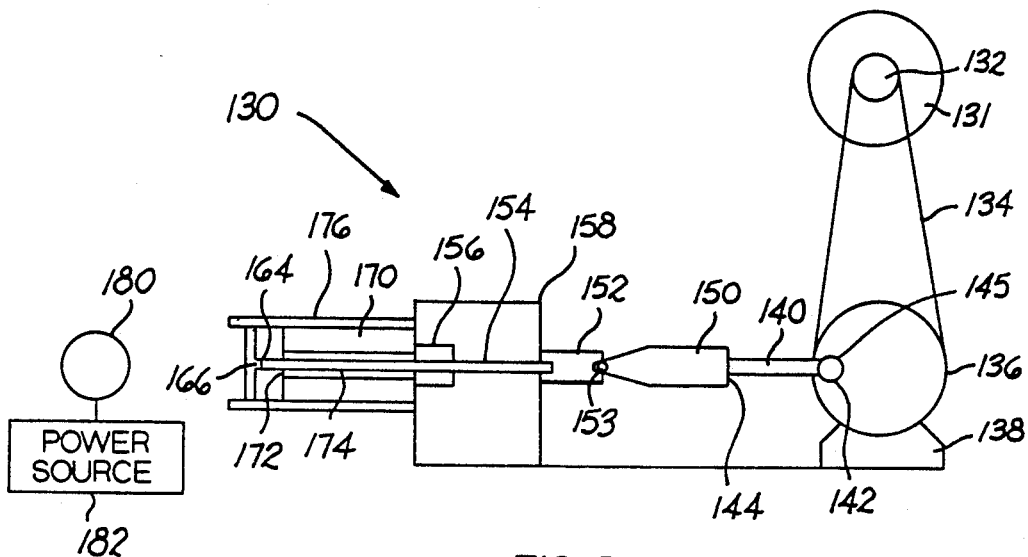
FIG. 5 is a mechanical schematic view of a third specific embodiment according to the present invention.

FIG. 5 illustrates a third specific embodiment of the invention, generally designated as 130. This embodiment includes a motor 131 which drives pulley 132. Pulley 132 is operatively connected through a belt 134 to an eccentric 136. Eccentric 136 rotatably mounts to the embodiment via a support 138.

A rod 140 has opposite ends 142 and 144. Rod 140 connects at its end 142 to eccentric 136. The point of connection 145 is near the circumference of the eccentric 136. Rod 140 connects at its end 144 to the Y-shaped end of a yoke 150. The other end of the yoke 150 pivotally connects to an insulator 152 at pivot point 153.

A rod 154 extends between insulator 152 and sensing probe 166. Rod 154 passes through an insulator 156. A metal electrostatic shield 158 is generally about a portion of rod 154 and insulator 156 so as to define a volume about this portion of rod 154 and insulator 156. The sensing probe 166 is at end 164 of rod 154.

A portion of rod 154 slides in a ceramic support 170. Ceramic support 170 is of a cylindrical shape with a central longitudinal bore 172. A cylindrical brass sleeve 174 is within bore 172. Rod 154 is in sliding contact with the brass sleeve 174.

A cylindrical housing 176 covers the ceramic support 170. The length of housing 176 is such that the sensing probe 166 is contained within the volume defined by housing 176.

In operation, the motor 131 operates to rotate pulley 132 which, in turn, drives belt 134 to rotate eccentric 136. The rotation of eccentric 136 causes the entire assembly, which eventually terminates with sensing probe 166, to reciprocate. This reciprocal movement is with respect to object 180 which causes a cyclic AC signal where the frequency is defined by the oscillation of the sensing probe. Object 180 has a surface charge thereon caused by the connection to power source 182.

Although not illustrated, a signal output may connect to the brass sleeve 174. The signal output may then connect to a high input impedance device that connects to a digital multimeter and chart recorder. An alarm system may also receive output from this device. This connection of the signal output to the monitoring devices is like that shown in the previous embodiments.

Although not illustrated in any of the specific embodiments, it is expected that a means to accurately measure the distance between the sensor and the surface of the charged object would be incorporated into a commercial embodiment of the invention. Such a measurement means could use acoustic sounding techniques such as those used on automatic focusing cameras, infrared technology or laser technology.

Applicants have conducted examples which are described below.

The equipment used for testing comprised a high voltage DC power supply with adjustable output for the static charge source, a high gain, high impedance input amplifier for the output signal amplification, a digital multimeter and a chart recorder for recording purposes.

EXAMPLE 1

This example illustrates the process of charge detection and measurement by using the specific embodiment shown in FIGS. 1 and 2. The experimental setup is shown in FIG. 2.

A 5.75" by 8.5" flat steel plate was connected to the positive output of the high voltage DC power supply. The sensing probe was made of a 1 cm by 1 cm brass plate. To eliminate the static charge generated from other sources, the apparatus and the steel plate were enclosed in a metal screen cage to assure accurate results.

The purpose of this experiment was to simulate a condition where the surface of the charged object is flat and much larger than the sensor. Hence, the results from this experiment can be applied to other flat surface objects such as surfaces of equipment in chemical plants and the like.

The measurements were done at various reference positions with different voltage input to the steel plate. The reference position was defined as the minimum perpendicular distance between the sensing probe and the charged steel plate.

Figure 6:
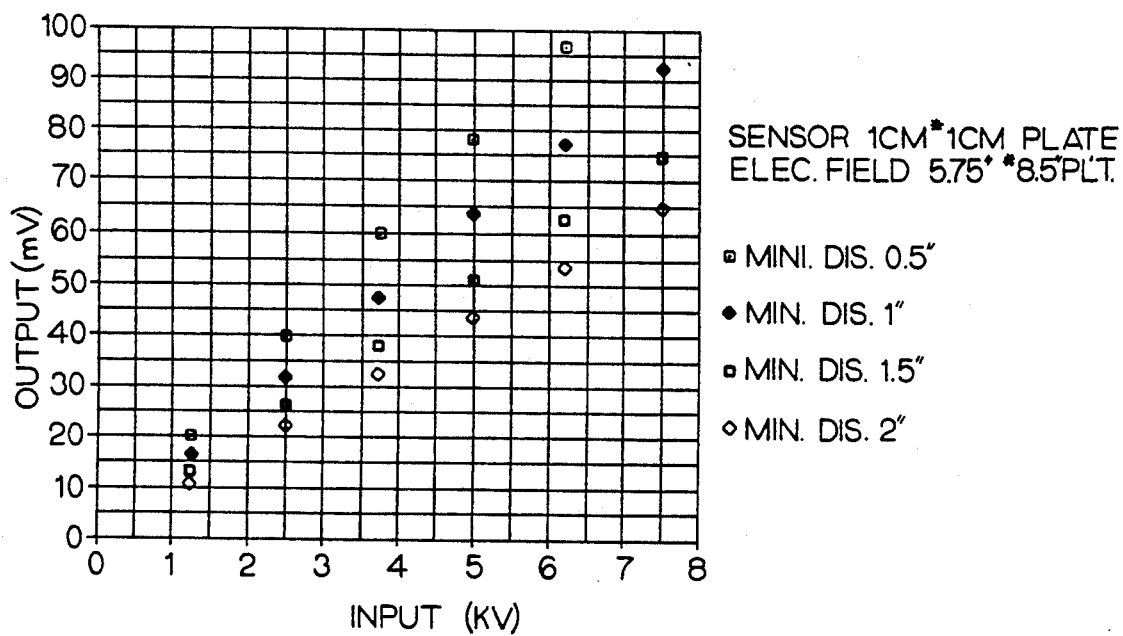
FIG. 6 is a chart of the output on the Y-axis and the input on the x-axis for experimental results using the first specific embodiment of the invention.

FIG. 6 shows the plot of the resulting data. The data shows that, for a given reference position, the output of the prototype is nearly proportional to the static potential input to the steel conductive plate. The proportionality of the data is kept well within 5% error through the whole range of measurements.

EXAMPLE 2

This example illustrates the process of charge detection and measurement by using the specific embodiment shown in FIGS. 3 and 4. The experimental setup is shown in FIG. 4.

A ⅜" steel ball was connected to the positive output of the high voltage DC power supply. The sensing probe is made of brass wire or rod 1/32" in diameter and 1.5 cm (0.59 inches) long.

The purpose of this experiment is to simulate the situation when the charged object is of the spherical or point type and the results can be applied to other charged spheres.

The measurements were done at various reference positions with different voltage input to the steel ball. The reference position was defined as the perpendicular distance between the centerline of the rotatable shaft carrying the sensing probe and the centerline of the charged steel ball.

Figure 7:
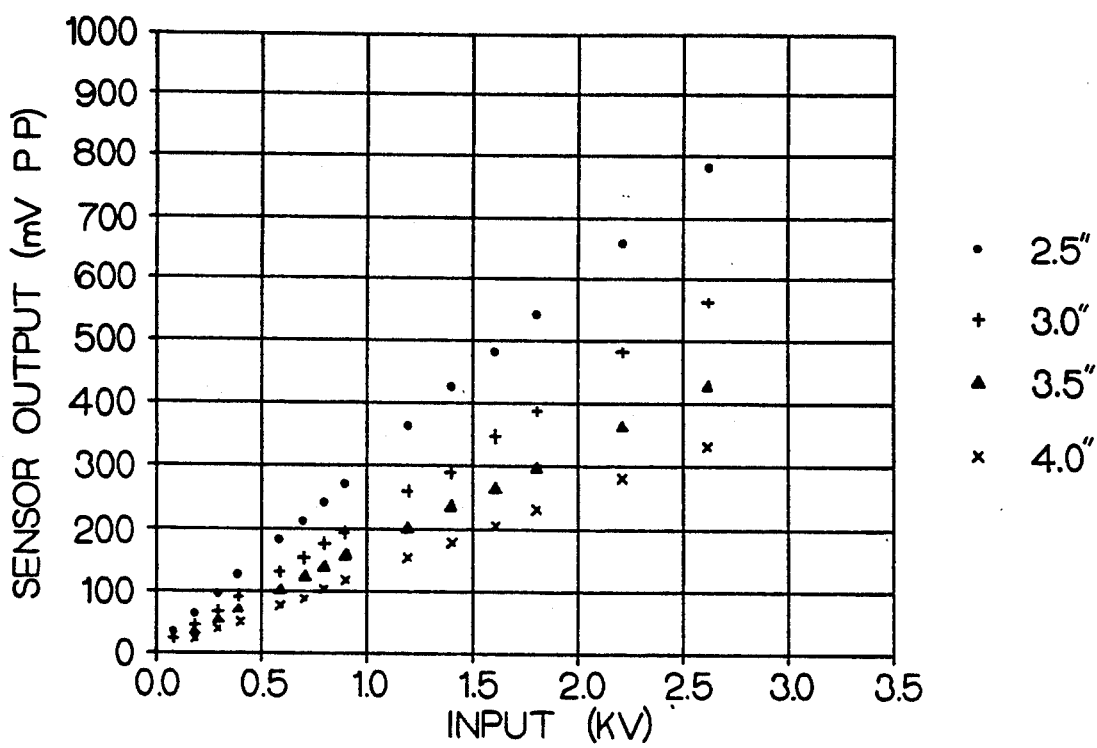
FIG. 7 is a chart of the output on the y-axis and the input on the x-axis for experimental results using the second specific embodiment of the invention.
Figure 8:
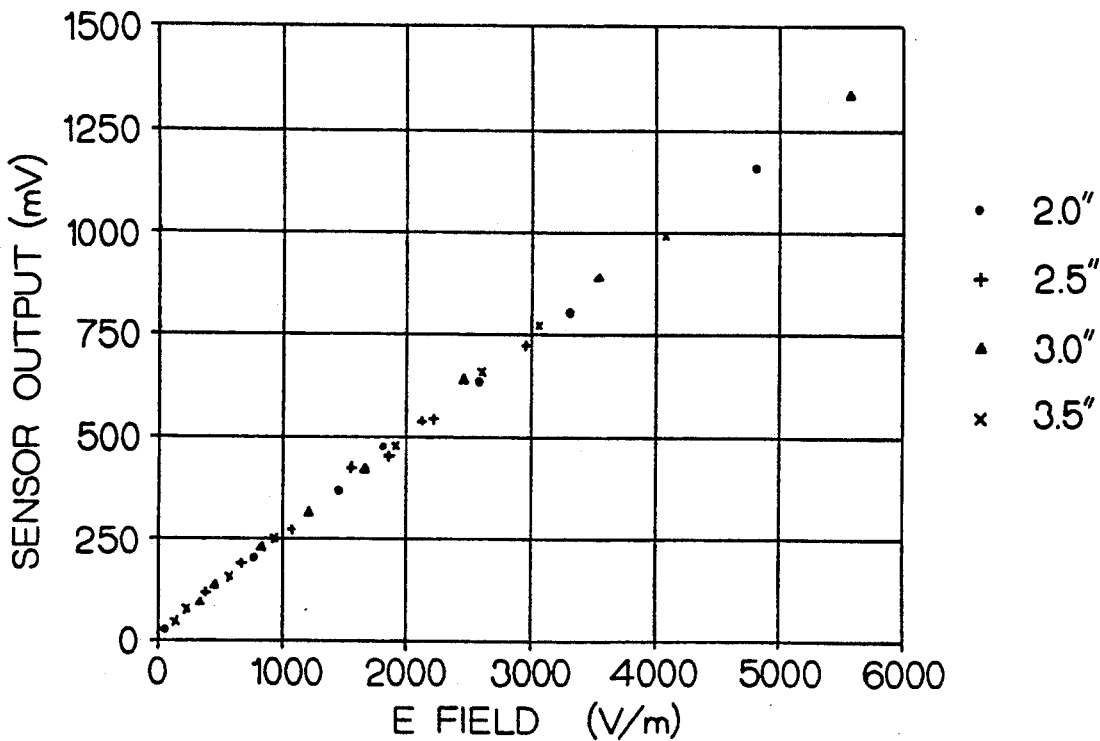
FIG. 8 is a chart of the sensor output on the y-axis and the field on the x-axis for the experimental results using the second specific embodiment of the invention.

FIGS. 7 and 8 show the plot of the resulting data. The data shows that, for a given reference position, the output of the prototype is nearly proportional to the static potential input to the steel ball. The proportionality of the data is kept well within 5% error through the whole range of measurements.

EXAMPLE 3

This example illustrates the applicability of this invention to measure the charge of a flat object, which is made of nonconducting material. The experimental setup is similar to the one shown in FIG. 2, except that the plate is made of acrylic. The static charge was generated through the rubbing of a wool fiber cloth on the surface of the plastic plate.

Figure 9:
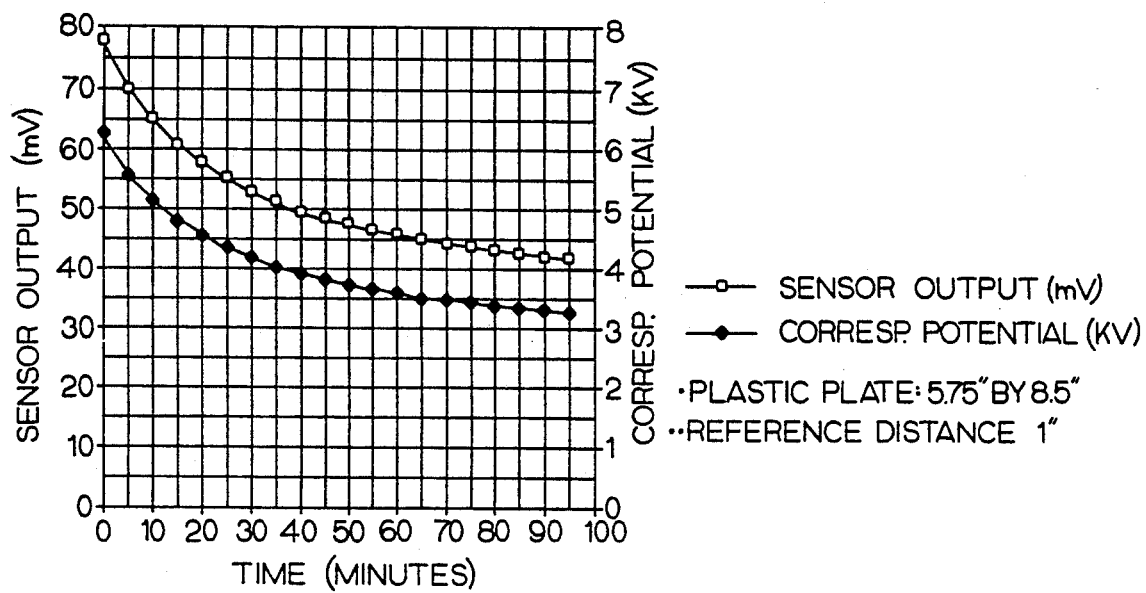
FIG. 9 is a chart showing the measurement of the discharge of a acrylic plate from Example 3.

The measurements were done at 1" reference distance. The discharge curve and corresponding static potential of the acrylic plate is shown in FIG. 9.

Based on the design concepts discussed above, we have now discovered and developed a new method and apparatus for charge detection and measurement. By applying a cyclic, relative motion between a conductor which is used as a sensor and the charged object at a reference distance, an AC signal can be detected on the sensor. Through proper calibration, the static potential of the charged object may be determined without any contact.

The ability to safely measure static charge on an object has many advantages. The actual measurement of the charge at any point in time is, of course, highly advantageous.

Another advantage is the ability of the invention to measure and monitor the static charge over time. In other words, the invention can detect the build-up or reduction of static charge on an object. The output can connect to another system which can sound an alarm indicating a preselected condition or activate a system to correct the existing condition.

While the invention has been described in detail and with reference to specific embodiments thereof, it will be apparent to one skilled in the art that various changes and modifications can be made therein without departing from the spirit and scope thereof.

We claim:

1. An apparatus for the detection and measurement of static electric charge on the surface of a charged object comprising:

a sensing probe, said probe being positioned a specific distance from the surface of the object;

a motor means, connected to the sensing probe, for providing cyclic movement to the sensing probe so as to cyclically move the sensing probe relative to the surface of the object; the motor means includes a clock motor, said clock motor connected to a wheel so that the motor rotates the wheel; and a monitoring means, connected to the sensing probe, for monitoring the potential of the charged object.

2. The apparatus of claim 1 further including a pivotal bar containing a slot, the wheel having a pin engaging the slot so that upon rotation of the wheel the bar pivots in a cyclical fashion.

3. The apparatus of claim 2 wherein a rod assembly connects the elongate bar to the sensing probe so that upon pivoting of the bar the sensing probe reciprocates in a cyclic fashion with respect to the surface of the object.

4. The apparatus of claim 3 wherein the rod assembly comprises an insulative rod connected to the elongate bar and a conductive bar affixed to the sensing probe, the insulative rod and the conductive rod operatively connected through an insulative linkage.

5. The apparatus of claim 1, wherein the motor means includes a motor with a rotatable shaft, the sensing probe being affixed to the distal end of the shaft so that the sensing probe rotates upon the rotation of the shaft under the urging of the motor.

6. The apparatus of claim 5 further including a contact that is in cyclic contact with the sensing probe.

7. The apparatus of claim of claim 1 further including an alarm means, connected to the sensing probe, for indicating a condition where the static charge has exceeded a preselected value.

8. The apparatus of claim 7 where the alarm means automatically discharges the surface of the object upon the static charge exceeding a preselected value.

* * * * *